United States Patent
Weissgerber et al.

(10) Patent No.: US 6,627,075 B1
(45) Date of Patent: Sep. 30, 2003

(54) DEVICE FOR AND PROCESS OF PREPARING VOLUME FLOWS OF LIQUIDS IN AT LEAST ONE PASSAGE OF A CHROMATOGRAPHIC COLUMN

(75) Inventors: Hans-Georg Weissgerber, Straubenhardt (DE); Hans-Peter Zimmermann, Karlsruhe (DE); Andreas Lorinser, Waldbronn (DE)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/538,252

(22) Filed: Mar. 30, 2000

(30) Foreign Application Priority Data

Mar. 30, 1999 (DE) .......................................... 199 14 358

(51) Int. Cl.[7] .............................................. B01D 15/08
(52) U.S. Cl. ..................... 210/198.2; 210/101; 210/659; 422/70
(58) Field of Search .............................. 210/198.2, 101, 210/656, 659; 422/70

(56) References Cited

U.S. PATENT DOCUMENTS

| | | | | | |
|---|---|---|---|---|---|
| 4,003,243 A | * | 1/1977 | Blu | .......................... | 210/198.2 |
| 4,174,772 A | * | 11/1979 | Neuss | ...................... | 210/198.2 |
| 4,840,730 A | * | 6/1989 | Saxena | .................... | 210/198.2 |
| 5,004,538 A | * | 4/1991 | Apfel | ....................... | 210/198.2 |
| 5,035,138 A | * | 7/1991 | Abdel-Rahman | ........ | 73/204.15 |
| 5,234,586 A | * | 8/1993 | Afeyan | .................... | 210/198.2 |
| 5,306,426 A | * | 4/1994 | Afeyan | .................... | 210/198.2 |
| 5,346,622 A | * | 9/1994 | Klee et al. | ............... | 210/198.2 |
| 5,491,096 A | * | 2/1996 | Sportsman | ............... | 210/198.2 |
| 5,614,089 A | * | 3/1997 | Allington | ................. | 210/198.2 |
| 5,938,932 A | * | 8/1999 | Connelly | ................. | 210/198.2 |
| 6,106,710 A | * | 8/2000 | Fischer | .................... | 210/198.2 |

FOREIGN PATENT DOCUMENTS

JP  4-115 158  *  4/1992  ............. 210/198.2

OTHER PUBLICATIONS

*Patent Abstracts of Japan*, JP–A2–4115158, P–1398, Aug. 7, 1992, vol. 16, No. 368.

* cited by examiner

Primary Examiner—Ernest G. Therkorn

(57) ABSTRACT

Volume flows of liquids in capillary tubes of chromatographic separation columns for analytical liquid measuring technology are controlled. The volume flows are derived from a liquid transport, i.e., pump arrangement, which transports a total flow to a flow splitter that divides the total flow into an excess flow in an excess path and a working flow in a working path. A controller for the working flow responds to at least one working sensor. The working sensor senses the mass flow rate of the working flow and/or the pressure in the working path which is coupled with the working sensor or the pressure differential in conduits for the excess and working flows.

24 Claims, 4 Drawing Sheets

DEVICE FOR AND PROCESS OF PREPARING VOLUME FLOWS OF LIQUIDS IN AT LEAST ONE PASSAGE OF A CHROMATOGRAPHIC COLUMN

FIELD OF INVENTION

The present invention concerns a device for and process of preparing volume flows of liquids in at least one passage of a chromatographic column, for analytical liquid measuring techniques.

BACKGROUND ART

Devices for preparing volume flows of liquids in capillary tubes are used in liquid chromatography, in particular high pressure liquid chromatography (HPLC). Depending on the internal diameters of the separation columns used, HPLC technology is divided into "normal bore technology" for separation columns with internal diameters in the range from approximately 3 to 5 mm, "micro bore technology" for separation columns with internal diameters in the range from approximately 1 to 2 mm, "capillary tube LC technology" for separation columns with internal diameters in the range from approximately 180 to 320 $\mu$m, and "nano LC technology" for separation columns with internal diameters of less than or equal to 100 $\mu$m.

For these applications, pump systems are required to generate or transport liquids at extremely small flow rates or volume flows. These liquids must be transported with high reliability and precision under the effective high pressures in the range of approximately 400 bar.

Two different methods are known at present for transporting and preparing liquids having such small flow rates in capillary tube separation columns for liquid chromatography.

A first method is based on the use of injection pumps. Injection pumps are special single-piston pumps. In contrast to conventional piston pumps, in injection pumps the pistons do not move to and fro during analysis but a single piston stroke takes place. Thus the liquid in an injection pump is always in transport mode. The pump chamber must therefore be dimensioned sufficiently large that a single transport stroke is sufficient for complete separation analysis. The pump chamber is pressurized before analysis as the piston in the pump chamber is pressed forward. During separation analysis no more suction is performed. With this process, a volume flow is possible which is independent of the elasticities within the pump chamber. The elasticities in particular of the seals, drive mechanics and elasticity due to the compressibility of the solvent can be compensated accordingly. A further advantage of injection pump technology is the high precision and reproducibility of the achievable volume flows. As the pump chamber is constantly under pressure during the transport phase, the volume flow essentially depends only on the resolution of the drive and the seal of the total system.

Injection pump technology however only has a low flexibility with regard to the achievement of different analysis times and the use of different column diameters. Both the possible analysis time and the selection of separation column diameter are dependent and limited by the maximum stroke volume of the injection pump available at the time the analysis is to be performed. Furthermore with an injection pump only one high pressure gradient at a time can be achieved. This means that each solvent involved in the analysis requires its own high pressure injection pump.

A further possibility for generating and preparing liquid volume flows in capillary tubes, in particular in chromatographic separation columns, for analytical liquid separating technology is the use of conventional piston pumps suitable for "normal bore technology" in connection with the so-called splitter technology. Here suitable flow splitters are used in order to divide the total flow generated and transported by the pumps into at least two part flows, an excess flow in an excess path and a working flow in a working path. The working flow required in the separation column is adjusted and provided by means of restrictors, i.e., by hydraulic resistances arranged in the excess path. The flow splitters and in particular the hydraulic resistances are usually constructed from "fused silica capillary tubes" with small internal diameters. The length and internal diameter of these elements determine the flow resistance. The total flow rate is divided according to the resistance ratios, where normally the smaller part flows through the separation column.

One advantage of this technology is the low production cost because the splitters and the hydraulic resistances can be produced by the users. The extremely small volumes inside the flow splitters or hydraulic resistances are advantageous here.

One particular disadvantage of the conventional splitter technology however is that the user receives no information on the amount of volume flow passing through the separation column during separation analysis. Therefore the volume flow must be measured in a complex manner with mini-injections using stop watches in order to be able to operate the separation columns efficiently. Furthermore even the smallest changes in flow resistance caused, for example, by a contaminated separation column frit, lead to a considerable change in the column flow, with the result of a correspondingly large retention time shift. In order to alleviate this effect, a hydraulic pre-resistance is sometimes inserted in the working path before the separation column. Thus with approximately the same pressure reductions in the separation column and the pre-resistance, the influence of a blocked separation column frit on the column flow is approximately halved. The use of such pre-resistances however means that only half the pump pressure is available for separation analysis in the separation column.

An object of the invention is to provide a new and improved device for and a process of providing volume flows of liquids in capillary tubes for analytical liquid metrology to achieve an essentially constant working flow volume of the liquid being analyzed independent of backpressure conditions.

SUMMARY OF THE INVENTION

This task is solved by the features of the claims, in particular in that the device has at least one working sensor and one control device to regulate the working flow rate and/or pressure in the liquid working path, where the control device is coupled to the working sensor and a means for changing the working flow rate. As a result, the working flow, i.e., the volume of liquid flowing through the capillary tube, can be kept essentially constant as a function of the pressure and/or volume conditions in the working path which change for example as a result of disturbance variables.

Suitably the means for changing the working flow volume is formed with a hydraulic resistance, in particular a nozzle. This allows smooth reproducible volume flows.

It is of particular advantage for the hydraulic resistance to have a flow resistance, in particular, to be continuously variable. Thus advantageously, variable hydraulic resistance values or "restrictions" can be set with a single hydraulic resistance. Depending on the pressure and/or volume flow conditions changing in the working path, by corresponding change of the flow resistance, the working flow volume and/or working pressure can be held constant. One particular advantage in using variable hydraulic resistances is that both a volume flow and a pressure control are possible in the working path. With pressure control, the pressure in the working path can be held constant irrespective of the solvent used. Constant pressure in the working path is always advantageous if the solvent in the working path must be changed quickly without allowing the working pressure to become too high. With maximum flow rates, constant pressure in the working path allows a considerable extension of the life of the delicate parts contained in the working path, for example the separation column.

A further advantage in using variable hydraulic resistances is that when correspondingly dimensioned, a very great range of achievable flow rates is possible. If an extremely small flow resistance is used, i.e., with high flow rates through the hydraulic resistance, it is possible to flush the entire device including a degasification unit with high flow rates normally used in "normal bore technology". This also allows correspondingly shorter flushing times. If a very high to infinite flow resistance is set, i.e., the volume flow through the hydraulic resistance tends towards zero, it is possible to use the device or separating system in a non-split mode. In the non-split mode, operation is possible which corresponds to that with a conventional piston pump.

A further advantage is that the total flow generated and transported by the transport device can be selected almost at will. A high flow rate allows a fast exchange of a dead volume between (1) a mixing point in the transport device formed for example as a pump, and (2) the capillary tube, which can be formed as a separation column. A high flow rate, at low pressure gradient operation, allows fast solvent change, i.e., faster gradients or short analysis times. In contrast when small total flow rates are set, large solvent quantities can be saved. Saving large solvent quantities is advantageous with regard to both environmental and cost aspects.

A further advantage of variable hydraulic resistances is that they can be formed as damping elements. When conventional piston pumps are used, on reversal of the piston short pressure impulses or pressure interruptions can occur. These impulses or interruptions can be compensated by suitably changing the hydraulic resistance, for example by brief closure thereof, with a controller. The pressure and/or volume flow fluctuations in the working path can thus be avoided without additional capacitative constructional elements.

As an alternative or in addition to the variable hydraulic resistances, the hydraulic resistance can also be formed with one or preferably plural fixed resistances which can be connected individually or in groups, preferably by a switching device, e.g., an electrically controlled valve. This valve can allow automatic connection of one or plural fixed resistances within an analysis frequency. The automatic connection can, for example, include a further control device and a further sensor, in particular a pressure sensor, allocated for example to the transport device or the total flow, as a function of the changing pressure conditions.

It is of particular advantage if the hydraulic resistance is arranged in the overflow path. Thus the required extremely small flow rates in the working path can be achieved flexibly at low cost with the required precision even under high pressures.

Alternatively or in combination with the use of hydraulic resistances, the working flow can be modified by a structure for changing the total flow, preferably with a transport device for transporting the total flow. If for example the resistance in the working path rises due to a blocked column inlet frit, the working flow in the working path is reduced accordingly. The total flow transported through the transport device can now be increased accordingly using the control device so that the working flow essentially remains constant.

Advantageously in this design, hydraulic resistances with modifiable flow cross sections and/or several hydraulic resistances with fixed resistances can also be used. In this way the total flow transported through the transport device can be varied within a narrower band.

Advantageously the device has one hydraulic resistance in the working path and one hydraulic resistance in the excess path. The hydraulic resistances are formed such that the working flow and the excess flow have different volumes. The working sensor includes at least one pressure sensor and a means for forming a pressure difference between pressures in the working path and excess path. Thus alone or in combination with other advantageous designs of the device, an essentially constant working flow volume can be achieved.

The volumetric measurement of the flow rates or volume flows necessary for liquid chromatography using capillary tube separation columns is extremely complex and difficult. This results in particular from the different physical properties of the different devices used and the occasionally very high pressures which can influence the measurement result. Volumetric flow meters for precise measurement of extremely small flow rates of liquids with different physical properties, for example with different compositions and/or concentrations, in capillary tubes for liquid measurement technology are not yet known. For these reasons, the working sensor is advantageously formed as a volumetric flow meter. A particularly advantageous volumetric flow meter for detecting the volumetric flow through the capillary tube can be achieved by forming the working sensor so it includes at least two detectors for detecting at least one gas bubble contained in the column flow. A time interval detector measures the run time differences of the gas bubbles passing the detectors.

It is known that mass flow sensors can detect minimum volume flows of liquids in capillary tubes. Such mass flow sensors, however, are always calibrated for only a single liquid or a single solvent and inherently function on a mass-selective basis. This means that the measurement result depends on the solvent used in each case. Suitable calibration of such mass flow meters for the different solvents used in liquid chromatography was previously either not possible or possible only with considerable expense.

According to a further particularly advantageous structure of the device, a hydraulic working resistance is arranged in the working path. Upstream of the hydraulic working resistance, a buffer device receives the liquids required for at least one calibration cycle. At least one pressure sensor measures the pressure or pressure drop over the hydraulic working resistance so that calibration of the working sensor is possible. The measurement value of the working sensor can be influenced by changing the physical properties of the liquids. The working sensor is preferably formed as a mass flow meter.

The device according to the invention enables simple and precise calibration of such mass flow meters, with regard to various solvents used during separation analysis. This results from the combination of a volume flow control and a pressure control. The volume flow and pressure controllers control a suitable means for modifying the working flow, a variable hydraulic resistance that is preferably continuously modifiable.

If the device contains a working sensor calibrated in this manner, essentially constant volume flows can be achieved in the working path even for liquids with physical properties which change, for example in gradient operation. In addition the user receives precise information on what volume flow is passing through the capillary tubes of the separation column which form a hydraulic resistance during separation analysis in the working path.

The invention also concerns a process of preparing volume flows of liquids in capillary tubes, in particular in chromatographic separation columns for analytical liquid metrology. A transport device transports a total flow which is divided by a flow splitter into an excess flow in an excess path and a working flow in a working path. A control device coupled with a working sensor and a means for changing the working flow volume govern the working flow volume and/or the pressure in the working path. Thus, independently of the back-pressure conditions, an essentially constant working flow volume can be achieved.

This process can be used particularly advantageously to calibrate working sensors in which a measurement value can be influenced by changing physical properties of the liquids. Such working sensors include a mass flow sensor in the working path. The sensor includes a hydraulic working resistance responsive to liquid flowing from a buffer device that receives the liquids required for at least one calibration cycle. At least one pressure sensor measures the pressure or pressure drop over the hydraulic working resistance. In a first step, a first liquid is transported in the working path and the volume flow of this first liquid is held essentially constant. The pressure sensor detects the pressure or pressure drop over the hydraulic resistance. In a second stage, the pressure or pressure drop over the hydraulic working resistance that was determined in the first stage is held essentially constant and a second liquid with physical properties different from those of the first liquid is transported in and through the working path at least until a working sensor can measure a corresponding measurement value. This measurement value allows calibration of the working sensor with regard to the second liquid.

Suitably the second step is performed several times in succession. In each case, the second step is performed with a third or last liquid which has physical properties different from the properties of the liquid previously transported through the working paths. Thus the working sensor can be calibrated simply and precisely for the liquid gradients required in liquid chromatography, for example HPLC technology.

Advantageously, the working sensor is calibrated by performing the first and second stages several times in succession, in each case with changed total pressures. Thus the working sensor can simply be calibrated precisely for different total pressures.

Suitably before the first stage and/or after the second or last stage of a calibration cycle, the working path is flushed with a first liquid. During flushing with the first liquid, the pressure or pressure drop over the hydraulic resistance is held essentially constant. Preferably during calibration cycle flushing, a greater total flow is transported or a higher total pressure is set. These measures allow fast and thorough flushing of the working path without the working pressure becoming excessively high. Consequently at maximum flow rates a considerable extension of the life of sensitive parts contained in the working path, for example, the separation column, is achieved.

The invention also concerns the use of a device with the features described above in capillary tube liquid chromatography.

The above measures contribute both individually and in combination to a particularly precise and reproducible separation result.

The above and still further objects, features and advantages of the present invention will become apparent upon consideration of the following detailed descriptions of several specific embodiments thereof, especially when taken in conjunction with the accompanying drawings.

DETAILED DESCRIPTION OF THE DRAWING

Figure 1:
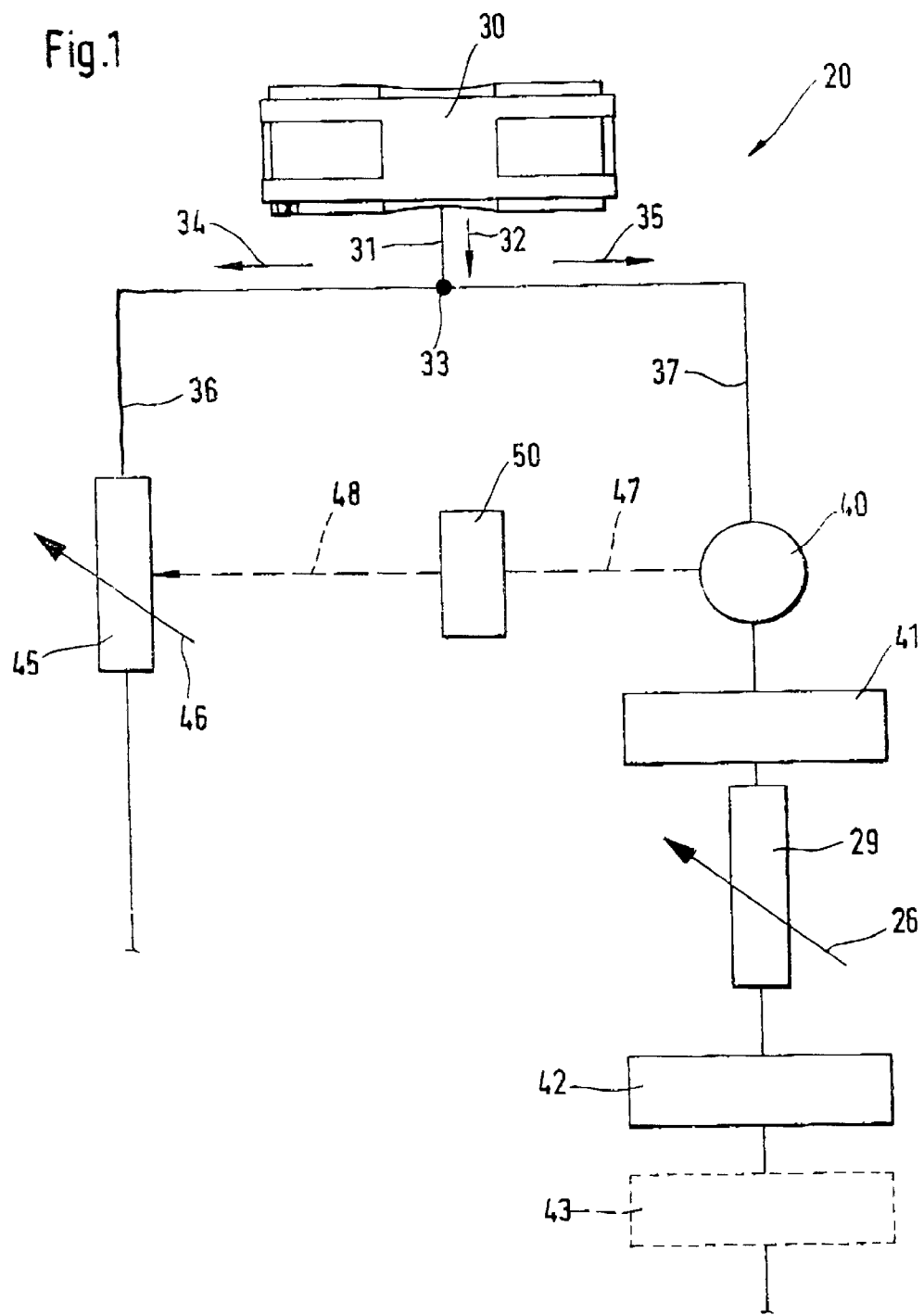
FIG. 1 is a diagrammatic view of a device according to a preferred embodiment of the invention, wherein a continuously variable flow resistance in the excess path changes the working flow.

FIG. 1 includes device 20 for preparing very small liquid volume flows in or through capillary tube 29 formed as a chromatographic separation column. The device 20 contains liquid pump 30 for transporting the total liquid flow 32 transported in the total conduit path 31. The pump arrangement 30 includes, in the case of gradient operation, both a high pressure pump and a low pressure pump.

The total flow 32 in conduit 31 is divided by a flow splitter 33 into excess flow 34 and working flow 35. The excess flow flows into excess path conduit 36 and the working flow 35 flows into working path conduit 37. Thus, there is a diversion at splitter 33 of the excess flow from the working flow. The excess flow is the difference between the total flow 32 transported by pump arrangement 30 and the working flow 35 required for separation analysis in the separation column formed as capillary tube 29. The excess flow 34 can, when a single solvent is used, be returned to pump arrangement 30 and is consequently available again. The excess flow 34 can also be diverted into a suitable catchment container.

Downstream in working path 37, connected to sensor 40, is specimen outlet 41 arranged immediately upstream of capillary tube 29. Arrow 26 indicates the continuously variable flow resistance properties of capillary tube 29, which is formed as a separation column.

Working sensor 40 is arranged in working path 37 upstream of capillary tube 29 and specimen outlet 41. Sensor 40 is preferably a thermal or thermally pulsed mass flow meter. Because working sensor 40 is on the high pressure side, upstream of specimen outlet 41, the effect of undesirable band broadening, i.e., a broadening of an originally narrow or defined sample peak, is minimized. Working sensor 40 can however also be arranged at any other suitable point in the path of working flow 35. Conventional detection devices 42 and 43, for example formed as UV detectors and/or as mass-selective detectors, are responsive to liquids in the separation column formed as one or more capillary tubes 29.

Excess flow conduit 36 is connected with continuously variable hydraulic resistance 45. The hydraulic resistance 45 is preferably formed as a nozzle with a continuously variable internal geometry. Depending on the setting of the flow cross section or the internal geometry of the hydraulic resistance 45, its flow resistance changes. Consequently the volume and flow rate of the excess flow 34 flowing through the hydraulic resistance 45 also changes. As a result the working flow 35 changes proportionally because the total flow 32 in conduit 31 remains essentially unchanged.

To control the mass flow of the working flow 35 flowing through the capillary tube 29 and detected by mass flow working sensor 40, the working sensor 40 is connected via line 47 with control device 50, in turn connected via line 48 with hydraulic resistance 45. Control device 50 of resistance 45 converts the mass flow measurement value detected by working sensor 40 according to the change in mass flow of working flow 35 into a signal for controlling hydraulic resistance 45 so the flow resistance of resistance 45 changes appropriately according to the modified flow and/or pressure conditions in the working path conduit 37.

In the design example shown in FIG. 1, pump arrangement 30 supplies conduit 31 with the approximately constant total flow 32, which is, for example, 240 $\mu$l per minute. Thus in the total path conduit 31, pressures up to 400 bar occur. A typical working flow 35 in a typical capillary tube with an internal diameter of 320 $\mu$m corresponds to 5 $\mu$l per minute.

Figure 2:
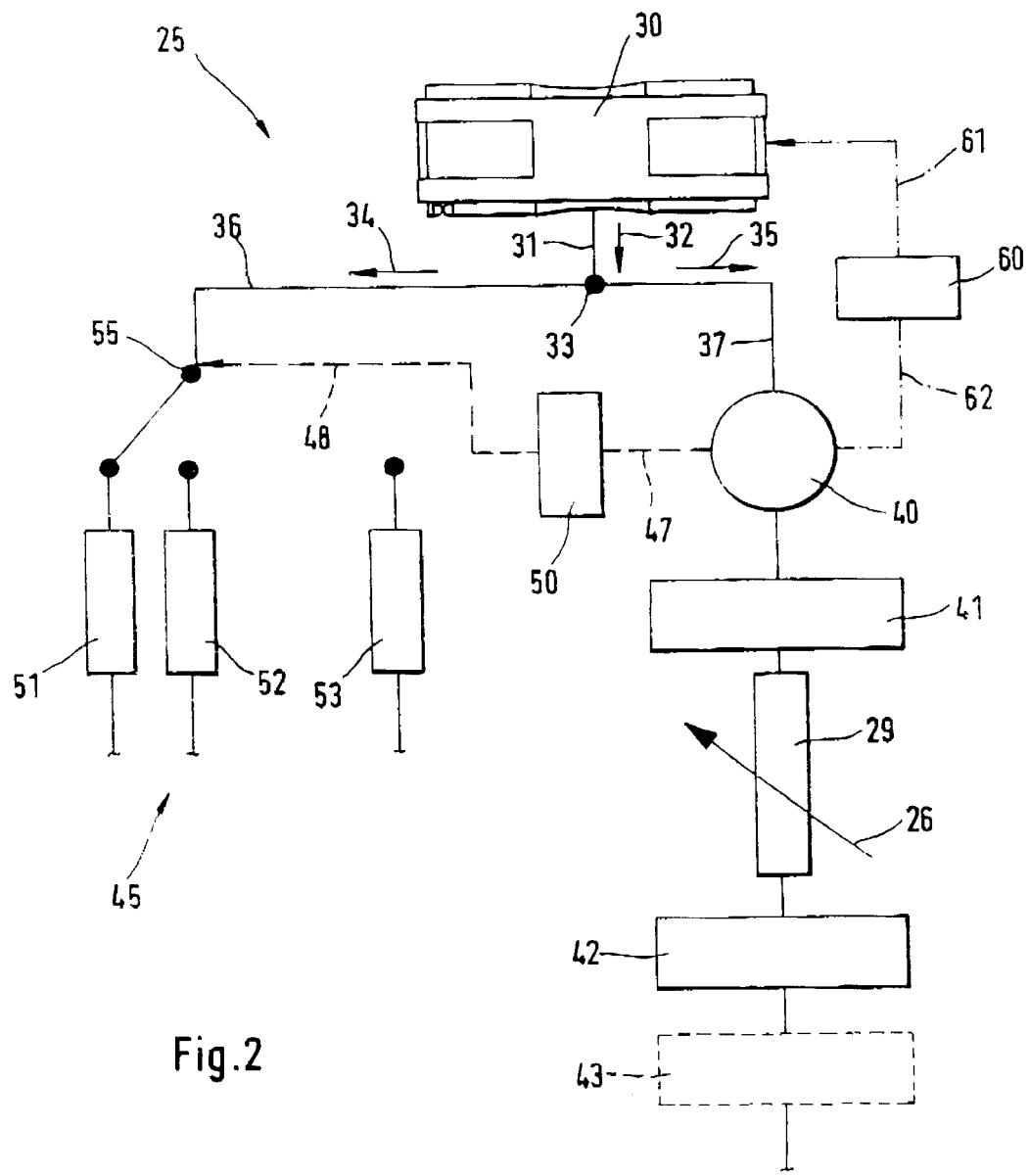
FIG. 2 is a diagrammatic view of an alternative embodiment of the invention, wherein several selectively switched hydraulic fixed resistances controlled by an electric switching valve replace the continuously variable resistance of FIG. 1. As a further means for changing the working flow, in this design example the transport device itself is formed as a pump for transporting a variable total flow rate.

FIG. 2 is a schematic diagram of a preferred alternative design example of the device 25. The same parts as in FIG. 1 are given the same reference numerals in FIG. 2. In contrast to the design variants shown in FIG. 1, the device of FIG. 2 contains several fixed hydraulic resistances 51, 52, 53 which can be switched individually or in groups into excess path 34. The connections of fixed resistances 51–52, 53 to excess flow conduit 36 are controlled by switching device 55 which in the design example is formed by an electrically controllable valve. Instead of the fixed resistances 51, 52, 53, continuously variable flow hydraulic resistance 45 can also be used.

In the same way as in FIG. 1, the hydraulic resistance in the excess channel 36 can be changed or modified using the control device 50 which is coupled via line 48 with the switching device 55 and via line 47 with working sensor 40.

The pumping arrangement 30 shown diagrammatically in FIG. 2 transports a variable total flow 32 to total flow conduit 31. The variable total mass flow in conduit 31 is typically in the range of 100 $\mu$l–500 $\mu$l, depending on the solvents used and the pressure in working path conduit 37. In the embodiment of FIG. 2, the mass flow of working flow 35 is controlled by both the hydraulic resistance 45, here formed as several switchable fixed resistances 51, 52, 53 and the mass flow that liquid pump arrangement 30 supplies to conduit 31. To govern the total flow 32 transported by pump arrangement 30 to conduit 31, mass flow rate control device 60 responds to the mass flow signal sensor 40 derives. Line 62 supplies controller 60 with the mass flow signal sensor 40 derives, while line 61 supplies pump arrangement 30 with the mass flow control signal controller 60 derives. This provides a particularly advantageous flexible operation of device 25.

Figure 3:
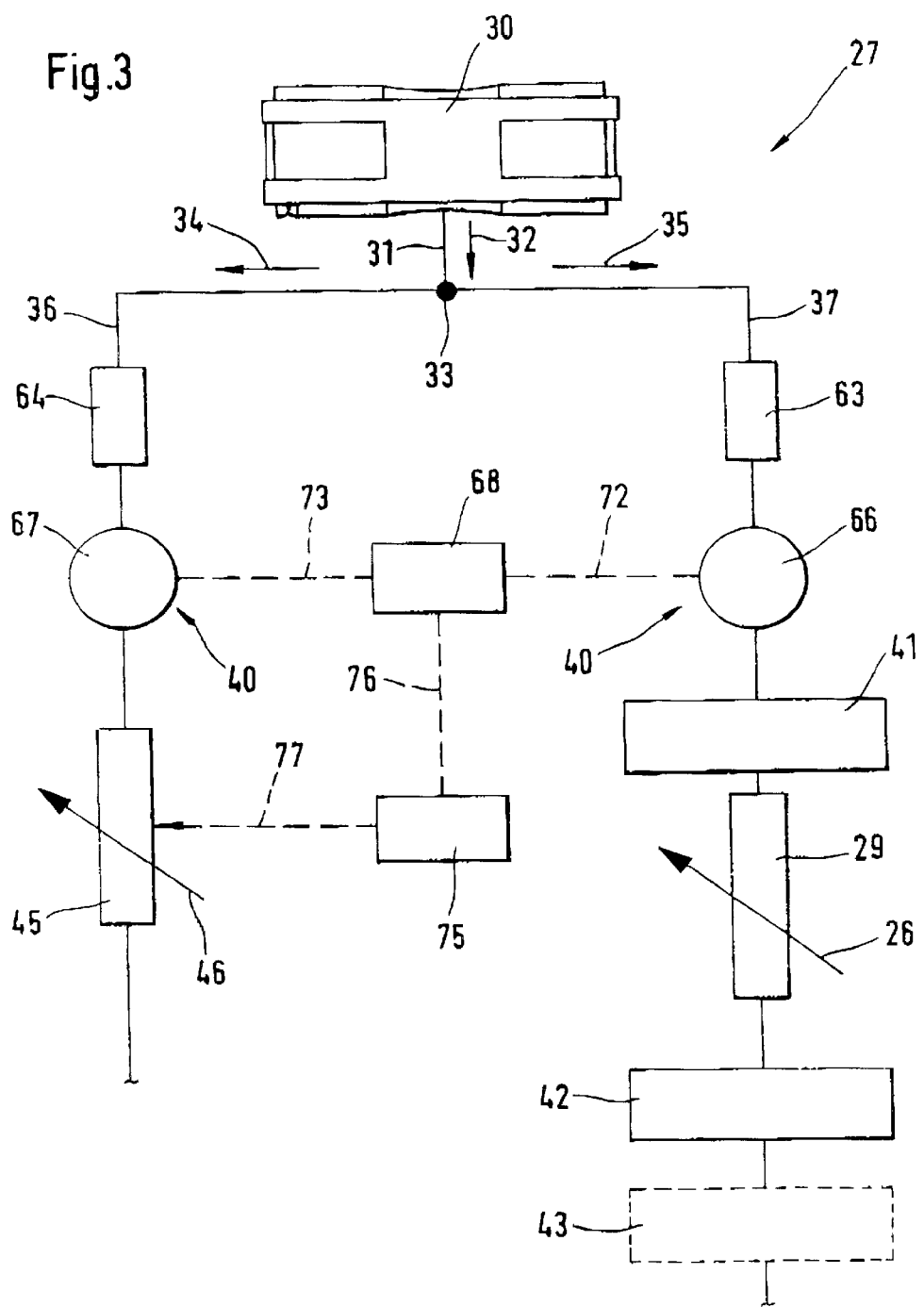
FIG. 3 is a diagrammatic view of a further design variant of the device where the working sensor includes first and second pressure sensors respectively arranged in the working path and in the excess path, in combination with a pressure difference formation means, wherein upstream in the working path and in the excess paths both include hydraulic resistances with different flow resistances.

FIG. 3 is a diagram of a further embodiment of a device according to the invention. The same parts as in FIG. 1 have the same reference figures in FIG. 3. The working sensor 40 includes pressure sensors 66 and 67 respectively in working path 37 and in excess path 36. Pressure sensors 66 and 67 supply signals to differential pressure sensor 68 via lines 72 and 73, respectively. Instead of the two pressure sensors 66 and 67, a single differential pressure sensor can also be used. The differential pressure sensor 68 derives an output signal that is coupled via line 76 with control device 75 which is coupled via line 77 with hydraulic resistance 45 having a continuously variable flow resistance. Upstream of pressure sensors 66 and 67 in working path conduit 36 and excess path conduit 37 are fixed hydraulic resistances 63 and 64, respectively. The hydraulic resistances 63 and 64 have different flow resistances which decisively determine the split ratio, i.e., the ratio of the part of the total flow 32 flowing through the working path 37 and though the excess path 36. Thus, fixed flow resistors 63, 64, differential pressure sensor 68 and variable, controlled flow resistor 45 are grouped into a hydraulic circuit analogous to an electrical Wheatstone bridge circuit.

Figure 4:
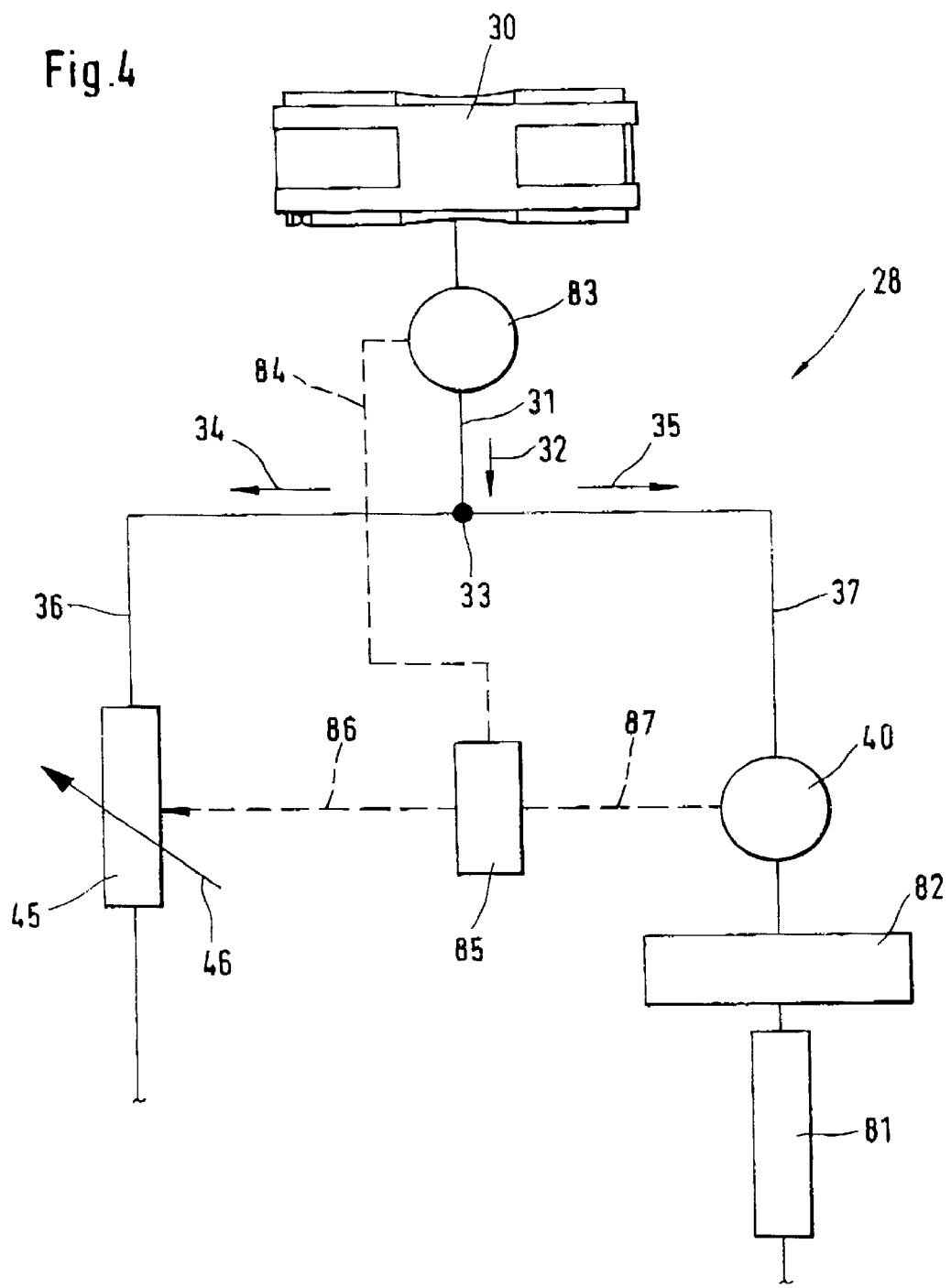
FIG. 4 is a diagrammatic view of a device for calibrating a mass flow sensor, i.e., a working sensor, the supply point signal of which is influenced by changing physical properties of the liquids.

FIG. 4 is a schematic diagram of a device 28 according to the invention for calibrating mass flow rate working sensor 40. Measurement value that sensor 40 of device 28 derives is influenced by changing physical properties of liquids flowing through it. The same parts as in FIG. 1 have the same reference numerals in FIG. 4.

To provide pressure-controlled regulation of the working flow 35 in the working path conduit 37, pressure sensor 83 monitors the pressure in total flow conduit 31. Sensor 83 can also be connected at other suitable points, for example in working path 37. An indication of the pressure that sensor 83 detects is coupled via line 84 to control device 85, having an output coupled via line 86 to hydraulic resistance 45 having a continuously variable flow resistance. To provide volume-flow-controlled regulation of working flow 35, control device 85 responds via line 87 to the mass flow rate signal working sensor 40 derives.

Buffer device 82 is downstream from working sensor 40 in working path conduit 37. Buffer device 82 safely holds the volumes of the liquids with different physical properties required during at least one calibration cycle. Thus, during the corresponding calibration cycle, these liquids cannot reach hydraulic working resistance 81, connected downstream from buffer device 82 and consequently cannot falsify the calibration result. The hydraulic working resistance 81 can, for example, be a fixed resistance or a chromatographic separation column.

The calibration of working sensor 40 is described in more detail below. To provide suitable calibration, a working sensor 40 is used which is precalibrated to a suitable calibration and flushing liquid. For many application cases, water has proved favorable as a calibration and flushing liquid. The working sensor 40 can, depending on the application conditions and the application concerned, also be precalibrated with other suitable liquids.

Before performing the calibration, a flushing phase is executed. During flushing, working path 37 is flushed with a first liquid, preferably water, for a time sufficient to remove from working path 37 all substances tending to falsify the calibration. Under pressure-controlled regulation, the pressure or pressure drop across the hydraulic resistance 81 is maintained essentially constant and flushing is carried out at high total pressures, for example at 300 bar, and high flow rates, for example 50 $\mu$l/min.

Then the actual calibration cycle begins under volume-flow-controlled regulation. A predetermined total volume flow rate of, for example, 5 $\mu$l/min, through conduit 31 is set and held constant. The total pressure in conduit 31 is reduced to a predetermined value, for example to 30 bar, to keep negligibly small the compressibility effect of the liquids. The pressure or pressure decrease occurring across hydraulic resistance 81 is measured and recorded.

The unit of FIG. 4 then switches to pressure-controlled regulation where the previously measured pressure or pressure reduction across hydraulic resistance 81 is set. Setting the pressure reduction across resistance 81 provides an essentially constant working mass flow rate of the liquids subsequently used in the working path. The mass flow rate of the liquids subsequently flowing in path 37 can consequently be held constant, independently of the physical properties of these liquids.

Then at a mixing point of liquids flowing into transport, i.e., pump, arrangement 30, a second liquid is added. Transport arrangement 30 pumps the second liquid until mass flow sensor 40 derives a measurement value corresponding to the volume of the second liquid supplied to transport arrangement 30. This measurement value provides a first calibration point characteristic of the second liquid under the selected other physical peripheral conditions. Then a third liquid is supplied to an inlet of transport arrangement 30 and transported in the same way as described above for the second liquid. This third liquid typically has a concentration and/or composition different from the second liquid. The third liquid is in turn transported through the working path 37 until the working sensor 40 derives a signal corresponding to the volume of the third liquid supplied to transport arrangement 30. This gives a second calibration point. In the same way further calibration points can be determined and registered.

The measurement values or calibration points are suitably stored using a storage device in the form of an electronic calibration table. This storage device is, for example, coupled via an electronic circuit to control device 85 so that the measurement values or calibration points are available for subsequent separation analysis.

At the end of a calibration cycle, depending on the working flow 35 which has flowed through the working path 37 during the calibration time, a specific liquid volume flows into buffer device 82. This liquid volume can be calculated before a calibration cycle is executed. The calculation provides minimum volume of buffer device 82 necessary to receive the entire liquid volume. The actual reception volume of buffer device 82 is selected to be sufficiently large to provide a safety volume in addition to the minimum volume. This measure can safely prevent the measurement liquid, i.e., the second and, where applicable, third or additional liquid volumes, from flowing into the hydraulic working resistance 81 to prevent falsification of the calibration result. Thus during a complete calibration cycle, only the first liquid flows through the hydraulic working resistance 81.

On completion of a calibration cycle, working path 37 is again flushed with the first liquid, i.e., here with water, as described above under pressure-controlled regulation of the working flow 35 until the entire liquid volume of the measurement liquid has flushed through the hydraulic resistance 81. Then a control measurement and/or separation analysis is performed.

The flow rate of the liquid through conduit 31 transported by transport arrangement 30 is held constant during the total calibration of the working sensor 40; for example, the total flow 32 through conduit 31 is 500 $\mu$l/min.

It is evident that on measurement, the entire volume flow from the mixing point (not shown) in transport arrangement 30 to working sensor 40 must be taken into account.

In the same way as described above, the working sensor 40 can easily be calibrated for different physical parameters which influence the physical properties of the liquids used. These parameters can, for example, be different total pressures and/or different volume flows.

As well as the design examples shown in the figures and described here, other design variants are possible which are adapted to the relevant user or measurement requirements. For example devices are possible in which the total flow 32 is divided not just into two but into several branches. The working sensor 40 can, for example, be downstream of detector 42. It is also possible to structure the working sensor 40 as a flow meter including (1) at least two spaced-apart detectors to detect at least one gas bubble contained in the working flow 35 and (2) a time difference detection means formed to measure the time differences of the gas bubbles passing the bubble detector or detectors. Such a time difference detector can be, for example, a differential amplifier. The gas bubble can be added from the outside or generated directly in the working flow 35. Such a volumetric flow meter has the great advantage that the actual flow can be measured independently of the solvents used.

We claim:

1. A device for preparing a small volume flow of a liquid in at least one passage of a chromatographic separation column arrangement for analytical liquid metrology, comprising a liquid transport device for transporting a total liquid flow to a liquid flow splitter for dividing the total liquid flow into an excess flow in an excess path and a working flow in a working path adapted to include the column arrangement so that all the divided liquid in the working path is adapted to flow in the column arrangement, a sensor for the liquid in the working path, and a controller coupled to be responsive to the sensor for controlling the liquid in the working path.

2. The device of claim 1 wherein the sensor is arranged for monitoring the mass flow rate of the working fluid and the controller is arranged for controlling mass flow rate.

3. The device of claim 2 wherein the controller includes at least one hydraulic flow resistor in the excess path connected to be responsive to the mass flow rate controller.

4. The device of claim 3 wherein the controller is connected to respond to the mass flow rate sensor for controlling the mass flow rate of the total liquid flow the transport device supplies to the flow splitter.

5. The device of claim 3 wherein the at least one flow resistor includes a continuously variable resistance connected to be controlled by the mass flow rate sensor in response to the sensed mass flow rate.

6. The device of claim 3 wherein the flow resistor includes plural fixed resistors selectively connected in the excess path to be controlled by the mass flow rate sensor to be responsive to the sensed mass flow rate.

7. The device of claim 2 wherein the controller is connected to respond to the mass flow rate sensor for controlling the mass flow rate of the total liquid flow the transport device supplies to the flow splitter.

8. The device of claim 1 wherein the sensor includes a pressure sensing arrangement responsive to the differential pressure in the excess and working paths.

9. The device of claim 8 wherein the controller includes a hydraulic flow resistor in the excess path responsive to the mass flow rate controller.

10. The device of claim 1 wherein the sensor includes a pressure sensing arrangement responsive to the pressure in the working path.

11. The device of claim 1 wherein the control device includes at least one hydraulic resistor.

12. The device of claim 11 wherein the at least one hydraulic resistor includes a nozzle.

13. The device of claim 11 wherein the at least one hydraulic resistor has a modifiable flow resistance.

14. The device of claim 11 wherein the at least one hydraulic resistor has a continuously variable flow resistance.

15. The device of claim 14 wherein the working sensor includes at least two detectors for detecting at least one gas bubble contained in the working flow, and a time difference detector for measuring the run time differences of the gas bubble passing the detectors.

16. The device of claim 11 wherein the at least one hydraulic resistor includes a fixed resistance.

17. The device of claim 16 wherein the at least one hydraulic resistor includes plural fixed resistors, the fixed resistors being switchable individually or in groups.

18. The device of claim 17 wherein the fixed resistances are switchable by a switch device.

19. The device of claim 11 wherein the at least one hydraulic resistor is in the excess path.

20. The device of claim 1 wherein the controller is arranged for changing the total flow flowing from the transport device to the flow splitter.

21. The device of claim 20 wherein the controller for changing the total flow includes a controller for the transport device for transporting the total flow.

22. The device of claim 1 wherein the working path includes a first hydraulic resistor and the excess path includes a second hydraulic resistor, the hydraulic resistors of the excess flow path and the working path being formed such that the working flow and the excess flow have different cross sectional areas, the working sensor including at least one pressure sensor and a differential pressure formation means for deriving an indication of the pressures in the working and excess paths.

23. The device of claim 1 wherein the working path includes a hydraulic working resistor, and a buffer device upstream of the hydraulic working resistor for holding liquid required for at least one calibration cycle, and further including a pressure sensor for measuring the pressure or pressure drop across the hydraulic working resistor for enabling calibration of the working sensor, the working resistor being of a type that the measured value thereof can be influenced by changing physical properties of the liquids.

24. The device of claim 23 wherein the working sensor includes a volume flow meter.

* * * * *